US012569630B2

(12) United States Patent
McCain et al.

(10) Patent No.: US 12,569,630 B2
(45) Date of Patent: Mar. 10, 2026

(54) METERED DOSE INHALER WITH MOUTHPIECE EXTENSION

(71) Applicants: Aisha McCain, Pittsburg, CA (US);
Annemarie Sheets, Pittsburg, CA (US)

(72) Inventors: Aisha McCain, Pittsburg, CA (US);
Annemarie Sheets, Pittsburg, CA (US)

(73) Assignee: Create To Overcome LLC., Pittsburg, CA (US)

( * ) Notice: Subject to any disclaimer, the term of this patent is extended or adjusted under 35 U.S.C. 154(b) by 885 days.

(21) Appl. No.: 17/883,119

(22) Filed: Aug. 8, 2022

(65) Prior Publication Data

US 2023/0045228 A1 Feb. 9, 2023

Related U.S. Application Data

(60) Provisional application No. 63/231,213, filed on Aug. 9, 2021.

(51) Int. Cl.
*A61M 15/00* (2006.01)

(52) U.S. Cl.
CPC ...... *A61M 15/009* (2013.01); *A61M 15/0023* (2014.02); *A61M 15/0065* (2013.01)

(58) Field of Classification Search
CPC ............ A61M 15/009; A61M 15/0023; A61M 15/0065; A61M 15/008; A61M 2205/18;
A61M 2205/3553; A61M 2205/3561; A61M 2205/3569; A61M 2205/3592; A61M 2205/505; A61M 2205/52; A61M 2205/581; A61M 2205/582; A61M 2205/583; A61M 2205/6054; A61M 2205/8206; A61M 15/0088
See application file for complete search history.

(56) References Cited

U.S. PATENT DOCUMENTS 7,703,454 B2 * 4/2010 Lee ...................... A61M 15/008
128/201.15
10,792,446 B1 * 10/2020 Baek ................. A61M 15/0023

* cited by examiner

*Primary Examiner* — Elliot S Ruddie
(74) *Attorney, Agent, or Firm* — Cynthia S. Lamon; Lamon Patent Services

(57) ABSTRACT

A metered dose inhaler includes ring body open at both ends, the ring body adapted to house a pressurized canister of medicine, an actuator ring including two or more external spring housings containing springs seated and aligned with spring seats formed on a cap attached to the distal end of the ring body the actuator ring fitting over the ring body in concentric fashion partially housing the ring body, the actuator ring having an actuator form fixed to an inside surface thereof to actuate a canister stem installed on the pressurized canister by urging the actuator ring against spring tension over the ring body toward the cap displacing a canister stem to break seal and dispense a dose of medicine.

20 Claims, 6 Drawing Sheets

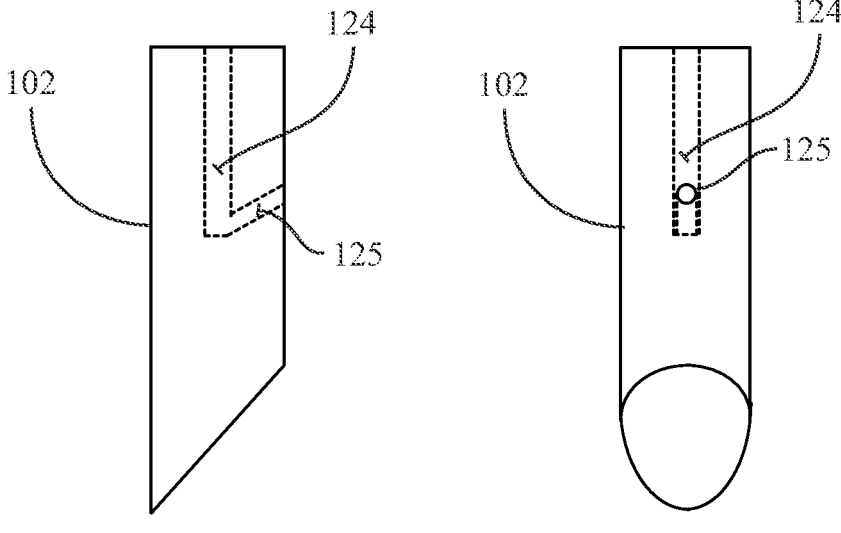
Fig. 6A                    Fig. 6B
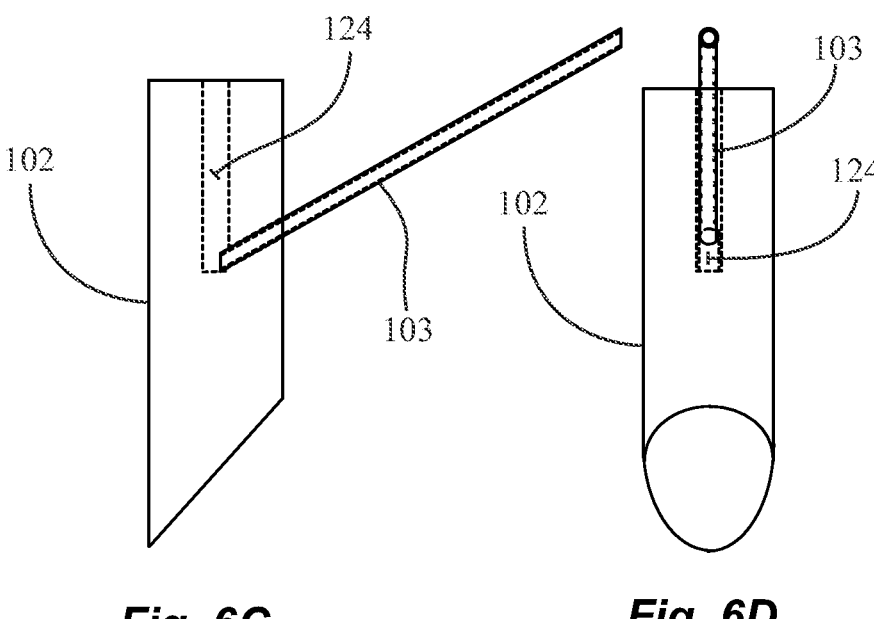
Fig. 6C                    Fig. 6D

METERED DOSE INHALER WITH MOUTHPIECE EXTENSION

CROSS-REFERENCE TO RELATED DOCUMENTS

The present invention claims priority to a U.S. provisional patent application Ser. No. 63/231,213, entitled "Portable Disc Inhaler with Telescopic Spacer" filed on Aug. 9, 2021, disclosure of which may be included herein at least by reference.

BACKGROUND OF THE INVENTION

1. Field of the Invention

The present invention is in the field of medical equipment and pertains particularly to a portable metered dose inhaler including a collapsible and retractable mouthpiece inhaler extension.

2. Discussion of the State of the Art

Asthma is a common, chronic respiratory disease that affects approximately 26 million people in the US. It is the most common chronic disease in childhood, affecting an estimated 7 million children. The estimate of lost work and school time from asthma is approximately 100 million days of restricted activity. Approximately 500,000 annual hospitalizations (40.6% in individuals aged 18 y or younger) are due to asthma. Each year, an estimated 1.7 million people (47.8% of them aged 18 years or younger) require treatment in an emergency department. For 2010, the annual expenditures for health and lost productivity due to asthma was projected to be $20.7 billion.

Patients with poorly controlled asthma develop long-term changes over time (i.e., with airway remodeling). This can lead to chronic symptoms and a significant irreversible component to their disease. Mortality in the US is approximately 1 per 100,000 and death often occurs in young people due to treatment and management failure. Medications for breathing problems, such as asthma and chronic obstructive pulmonary disease (COPD), are commonly delivered directly to the lungs. These medications include albuterol and steroids, among others. The device to deliver these medications is called an inhaler. Most of the devices are more specifically referred to as Meter-Dose Inhaler (MDI). Critically, albuterol delivered by MDI is the fastest way to reverse an asthma attack. The medicine allows the muscles around branches of the lungs to relax.

When using a MDI, patients must be able to breathe out, put the inhaler in their mouth, then inhale while activating the MDI actuator. The medication is in the form of aerosol and needs to be inhaled with close coordination. This can be challenging for anyone, but especially for children. Many times, the medication ends up in the mouth, the back of the throat, and is swallowed instead of being inhaled. In order to ensure that the medicine is actually inhaled, an extension accessory for the mouthpiece is strongly recommended. Such an extension may be referred to as a spacer in the art consisting of a chamber or large tube which attaches to the mouthpiece of the MDI.

The patient inhales through the mouthpiece of the spacer. In this arrangement, the patient activates the MDI actuator, filling the chamber of the spacer with aerosol such as albuterol which is then inhaled by the patient. The use of spacers has been shown to increase the amount of medication that is delivered to the lungs. Despite the clear and proven benefits of spacers, many patients do not take keep their spacer with them because they are bulky and awkward, easily forgotten or lost.

Therefore, what is clearly needed is portable MDI with a mouthpiece extension that overcomes the challenges cited above with current spacer type accessories.

BRIEF SUMMARY OF THE INVENTION

According to an embodiment of the present invention, a metered dose inhaler is provided including a ring body open at both ends, the ring body adapted to house a pressurized canister of medicine, an actuator ring fitting over the ring body in concentric fashion partially housing the ring body, the actuator ring having an actuator form fixed to an inside surface thereof to actuate a canister stem installed on the pressurized canister, at least two annular spring housings fixed to the outside surface of the actuator ring, the spring housings extending longitudinally thereon, in parallel, and equally spaced apart around a three hundred and sixty degree perimeter, at least two industrial springs inserted one each into the at least two annular spring housings the springs anchored thereto, a thumb hold ring disposed concentrically about the distal end of the actuator ring, the thumb hold ring including a concentric raised ring feature formed on the wall surface thereof, a collapsible and extendable spacer cone installed over the raised ring feature, a first cap for capping the ring body to cover the canister, the first cap including at least two spring seats for seating the at least two industrial springs, and a second cap for capping the spacer cone in a collapsed state.

In one embodiment, the ring body has a variety of electronics embedded in the material thereof. In this embodiment, a portion of the variety of electronics are partially embedded in the material thereof and remain visible from the outside of the ring body. In a preferred embodiment, the actuator ring has a double walled construction and fits over the ring body concentrically, the ring body partially housed by the actuator ring. In one embodiment, the actuator form is triangular and has a uniform wall thickness. In this embodiment, the actuator form is disposed on the inside surface of the actuator ring in alignment with the canister stem housed inside the ring body. Also in this embodiment, the canister stem has an angled end that interfaces flush with the presented face of the triangular actuator form.

In one embodiment, the springs are snapped into the spring seats on the first cap when assembled and aligned. In one embodiment, the end cap and the ring body each have alignment marks that provide a means for aligning the cap to the ring body. In this embodiment, the actuator ring is aligned to the ring body by aligning the spring positions to the correct spring seats. In a preferred embodiment, the actuator ring is urged over the ring body causing the actuator form to make contact with the canister stem to displace the canister stem into the canister breaking seal thereby actuating a dose of medicine.

In one embodiment, the canister stem has a first longitudinally centered bore in communication with the canister and a second bore intersecting the first bore at an acute angle the second bore accepting an aerosol stem inserted therein. In the embodiment including various forms of electronics, one of the variety of electronics in the ring body is a microprocessor with wireless connection capability. In one aspect of this embodiment, the wireless connection is Bluetooth and the MDI can be located by another Bluetooth device. In another aspect of the embodiment, the wireless connection is radio frequency identification (RFID) and the metered dose inhaler can be located by a freight on board (FOB) device.

In all embodiments, the spacer cone includes a mouthpiece at the distal end and is stretched over the Raised ring feature of the thumb hold ring. In a preferred embodiment the second cap locks over the thumb hold ring with the spacer cone collapsed. In this embodiment, the spacer cone is collapsed when the metered dose inhaler is idle and is extended for use. In a preferred embodiment, the spacer cone has the same internal volume as the canister when extended. In another embodiment, the spacer cone is carried separately from the metered dose inhaler in a collapsed state and is installed by a user when required.

BRIEF DESCRIPTION OF THE SEVERAL VIEWS OF THE DRAWINGS

FIG. 6A is a side view of the canister stem of the canister of FIG. 1.

FIG. 6B is a front view of the canister stem of FIG. 6A.

FIG. 6C is a side view of the canister stem of FIG. 1 with the aerosol stem of FIG. 1 inserted therein.

FIG. 6D is a front view of the canister stem of FIG. 6C with the aerosol stem of FIG. 6C.

DETAILED DESCRIPTION OF THE INVENTION

In various embodiments described in enabling detail herein, the inventor provides a unique metered dose inhaler (MDI) with a collapsible and retractable mouthpiece extension also referred to herein as a spacer device for short terminology. The present invention is described using the following examples, which may describe more than one relevant embodiment falling within the scope of the invention.

A goal of the invention is to provide a metered dose inhaler (MDI) in a disk configuration coupled with a collapsible and retractable spacer device attached thereto and removable therefrom.

Figure 1:
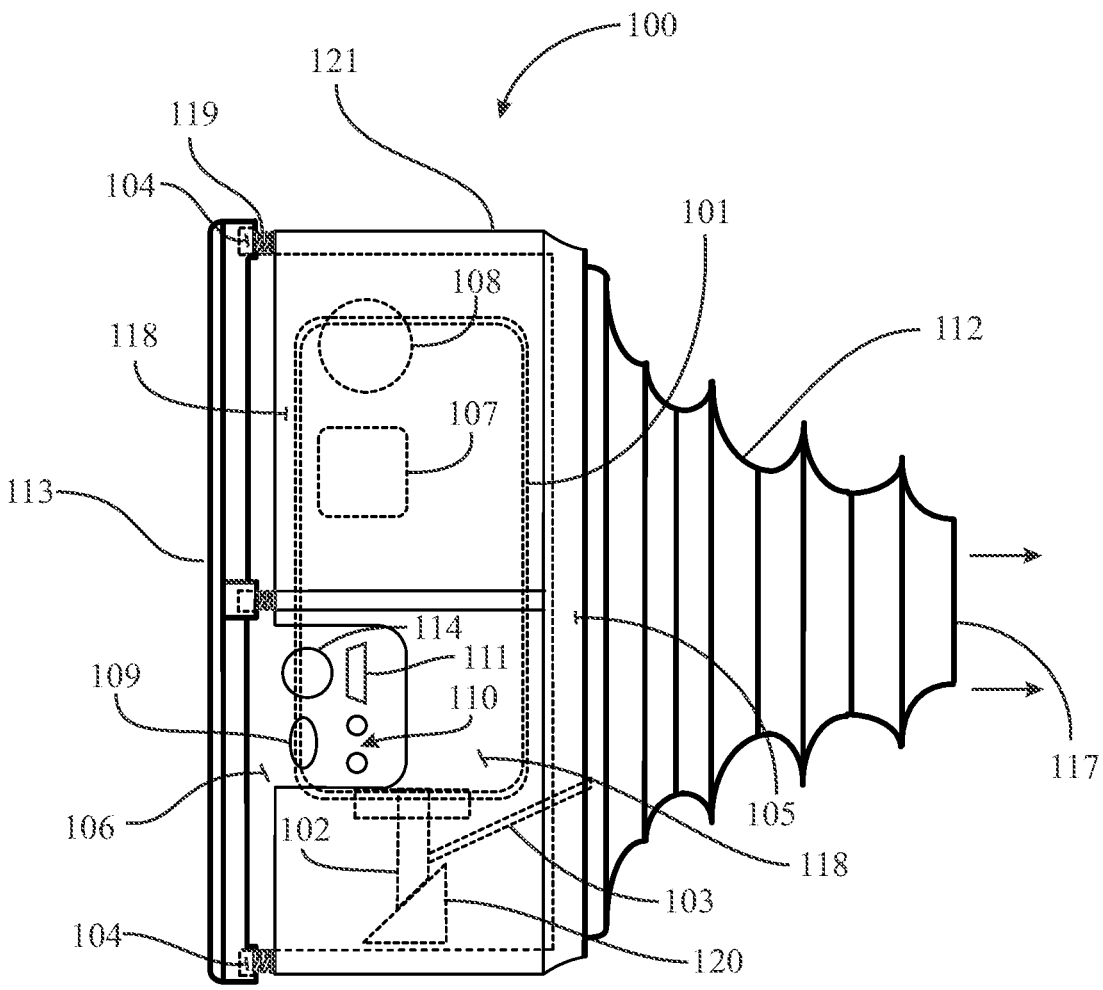
FIG. 1 is a side view of a portable MDI with a mouthpiece extension according to an embodiment of the present invention.

FIG. 1 is a side view of a portable MDI 100 with a mouthpiece extension according to an embodiment of the present invention. MDI 100 is annular in general form much like a disk configuration. MDI 100 is an assembly and includes a ring body 106 in the form of a cylinder having an inside and outside diameter. Ring body 106 may be manufactured from a high grade medical plastic. Ring body 106 forms a housing for a nested MDI canister 101. Canister 101 may be a standard pressurized medicine canister that may be modified using a proprietary stem to dispense one or more metered doses via intentional breach of a pressure seal on the dispense end of the canister according to an embodiment of the present invention.

In this embodiment, MDI canister 101 has a central activator stem 102 that is angled on the free end to match the angle of an actuation bar fixed to the inside diameter surface of an actuator ring 118 that, in this embodiment, has a double-walled configuration that enables ring body 106 to be concentrically inserted into the space between the double walls of the activator ring 118. Activator ring 118 may be manufactured of medical grade plastic. Activator stem 102 includes a central passage to a removable aerosol stem 103 that directs the dispensed medicine at an angle off vertical toward a mouthpiece extension device of the MDI and into the inner volume of the extension device referred to herein as a collapsible spacer device 112 or simply spacer 112. Actuator stem 102 and aerosol stem 103 may be manufactured of high grade medical plastic. Actuator stem 102 may be provided as a replacement stem for a standard MDI canister stem. Actuator stem 102 may also be provided as a standard stem for MDI canister 101 to work with MDI 100.

Actuator ring 118 is open at the end thereof that interfaces with ring body 106. Actuator ring 118 includes an inwardly-angled thumb and finger hold ring 105 that may be materially contiguous with the actuator ring 118. Hold ring 105 provides an ergonomic surface for a user of MDI 100 to initiate an active dose dispense event. Spacer 112 may be attached to actuator ring 118 at a concentric ring feature formed on the rear surface of hold ring 118 of MDI 100. Spacer 112 may be manufactured of a silicon based flexible but resilient material such as a high grade medical silicon rubber. Medical grade material may withstand high temperature sterilization procedures and may be food grade and free of BPA chemicals. Spacer 112 is conical in form and includes a mouthpiece form 117 at the free end thereof. Mouthpiece 117 is designed to fit comfortably over the mouth of an adult or the mouth and nose of a small child.

Spacer 112 may be attached to MDI 100 by stretching the larger opening of the spacer over the ring feature (not visible) on the surface of hold ring 105 of actuator ring 118. Spacer 112 may be collapsed flat against itself by pushing it in toward the MDI assembly. Spacer 112 may also be retracted out to extend outward using moderate pull force to set the full internal volume within spacer 112. Spacer 112 may have an internal volume of approximately ~130 ml, which is the same standard volume in MDI canister 101. The larger diameter of spacer 112 may be about 4 centimeters (cm). Spacer may be sterilized with other MDI components at high temperatures to ensure hygienic use. In this embodiment ring body 106 and actuator ring 118 are aligned and assembled for operation, and spacer 112 is fully retracted to extend outward as depicted by a pair of directional arrows. In all embodiments, spacer 112 may be collapsed for practical every day carry and can easily attach to fobs, keys, and bags with a carabiner or lanyard.

In this embodiment, actuator ring 118 includes external annular spring housings 121 oriented longitudinally and equally spaced about the diameter thereof. Each spring housing 121 may support an industrial spring 119. In this embodiment, there are four spring housings 121 and four springs 119 in the MDI assembly, however there may be only two, three, or more such as five or six spring housings holding springs symmetrically arranged about the outside of actuator ring 118. Spring housings 121 may extend to the end (edge) of actuator ring 118. Springs 119 may be anchored at the rear of the spring housing and may extend a distance further out of the housing. Cap 113 may be installed to ring body 106 and removed therefrom to access and change the canister to the spring housing pattern on actuator ring 118. Cap 113 may be manufactured of high grade medical plastic and may snap onto the canister access end of ring body 106. Cap 113 remains in place during dosing operation. In this embodiment, cap 113 includes a flange area that extends out in diameter and that includes a number of spring seats formed therein equal to the number and spacing pattern of spring housings 121. Springs 119 may each snap into the respective spring seats 104 on cap 113 so the assembly remains intact and aligned for use.

A second protective cap is provided to cap the opposite end of MDI 100 but is removed in this view for access and extension of spacer 112. Springs 119 may all have equal tension applied when an operator urges actuator ring 118 toward cap 113 using thumb/finger hold 105 to urge the actuator ring forward on the MDI assembly. Finger/thumb hold ring 105 may be formed peripherally about the base end of the actuator ring and may be a contiguous form made of the same material as the actuator ring.

Actuator ring 118 includes an actuator triangular form 120 strategically located on the inside surface of the actuator ring in alignment with activator stem 102. Actuator triangular form 120 is triangular inside profile, of uniform material thickness, and has a front face angled at the same angle as the angled free end of actuator stem 102. In one embodiment, the angle is approximately forty five degrees. In this way, an operator may urge actuator ring 118 forward against spring tension to bring actuator triangular form 120 into a contact position with activator stem 102 of canister 101 to cause it to break seal and deliver a dose of medicine that travels out through aerosol stem 103 and into the internal volume of spacer 112. The user may the aerosol medicine through spacer mouthpiece 117 at the end of the extended spacer device 112. Mouthpiece 117 replaces a standard MDI mouthpiece in this embodiment as ring body 106 is open on that end.

MDI 100 includes a variety of electronics embedded or otherwise installed to or attached to ring body 106. Ring body 106 may be about 2.5 mm to 3 mm thick enabling embedded components described as electronics. The purpose of electronics embedded within MDI 100 serves primarily in enabling a user to find MDI 100 if it is misplaced. In this embodiment, ring body 106 includes a microprocessor 107 adapted for Bluetooth™ or Bluetooth Lite™ wireless communication enabling wireless communication with another Bluetooth™-enabled device operated by a user/operator such as a mobile phone, for example. Microprocessor 107 may support limited computer-aided processing including wireless communication through Bluetooth™ LE, and or radio frequency identification (RFID), FOB contact, or any similar wireless communications technology. Microprocessor 107 may be powered using one or more Li-ion rechargeable batteries (not illustrated) having trace connections to other power consuming components. Ring body 106 may include an embedded or partially embedded speaker 108 that may make a sound, a beep, or some other amplified noise when MDI 100 is located via a Bluetooth™ signal. In one embodiment, ring body 106 of MDI device 100 includes an eccentric rotating motor (ERM) 109 that may be powered to vibrate or buzz in a silent mode in a case whereby speaker 108 may be muted in selective mode available on MDI 100 as a selectable configuration option.

In one embodiment, electronics in ring body 106 may include a Sims card (not illustrated) enabling telephony such as one way alert or messaging on the device with respect to one or a limited number of call target phone numbers/message that might be programed into a memory device on the microprocessor 107 device by a user. In case of more than one call target, a scroll function may be added such as a button scroll and LED display to enable a user to bypass calling one number to call another number. It may be noted herein that actuator ring 118 may be modified by material relief for the purpose of not covering any electronics components that are visible or need to be accessed on the outside surface of ring body 106. Actuator ring 118 may be shorter in ring depth than ring body 106 to allow for a slight gap space for spring compression and dose activation.

In one embodiment, an emergency call button 114 may be provided to enable a user to activate emergency calling/messaging in case of an emergency. Ring body 106 of MDI device 100 may include a pair of light emitting diodes (LEDs) 110. One LED may be a white light while another LED may be a red light, for example, arrayed adjacently and visible from the outside of ring body 106. In one embodiment, LEDs 110 may be adapted to flash alternately or in specific patterns to create a visual notification upon receiving a signal from a wirelessly paired FOB device or a Bluetooth™-enabled mobile device. In one embodiment, LEDs 110 may provide information relative to charging state of the compliment of electronics in ring body 106.

Colors of LEDs may vary such as green and red, green and white, etc. LEDs may be actuated by a wireless signal and or by an internal state notification command from microprocessor 107. Relative to device charging, ring body 106 of MDI 100 may include a micro universal serial bus (mUSB) charging port 111 that enables MDI 100 to be charged using a remote device like a laptop computer connected to the MDI device by a USB charging cable. In other embodiments, other charging schemes and hardware might be used in addition to or in place of USB without departing from the spirit and scope of the invention.

In general, the mentioned electronics embedded or attached to ring body 106 may further include a global positioning satellite (GPS) module, a user operable help button with (network access), and an internal memory or secure digital (SD) card that is accessible to the operator and may store data about the patient and owner of the MDI device 100. GPS may enable a user to locate an inhaler remotely using a network connected device like a cellular phone. A user operable help button (in addition to button 114) may be provided and integrated into the ring body and may be adapted to enable a user to send an alert by depressing the help button. Such an alert may be sent wirelessly to a targeted network access point, for example, a patient support service or an emergency dispatch system. The alert may denote a life-threatening emergency and may cause rescue to use GPS to locate the operator by locating the MDI device 100.

It is noted herein that a freight on board (FOB) device might use BT/RFID to locate MDI 100. In one embodiment, MDI device 100 may include a memory that is accessible through the micro USB charging port 111 from a computing device. A user or operator may update patient data or medicine availability data or store other important data like medicine canister type and availability data, use state of the inhaler device (use counter), or other data deemed important to store in the memory. In one embodiment firmware (FW) may be provided along with operator ability to access and perform updates including replacing FW on the microprocessor and in some embodiments, other processing chip components. In one embodiment, an FOB device may employ Bluetooth/RFID executed by a user depressing an FOB button to locate MDI 100 as described further above. In one embodiment, a user may leverage the USB connection and an application executing on a mobile device, configure the alert notification features selecting which features or combination of features sound, vibration, and or visible light, to activate and which if any to moot on the MDI device 100.

Figure 2:
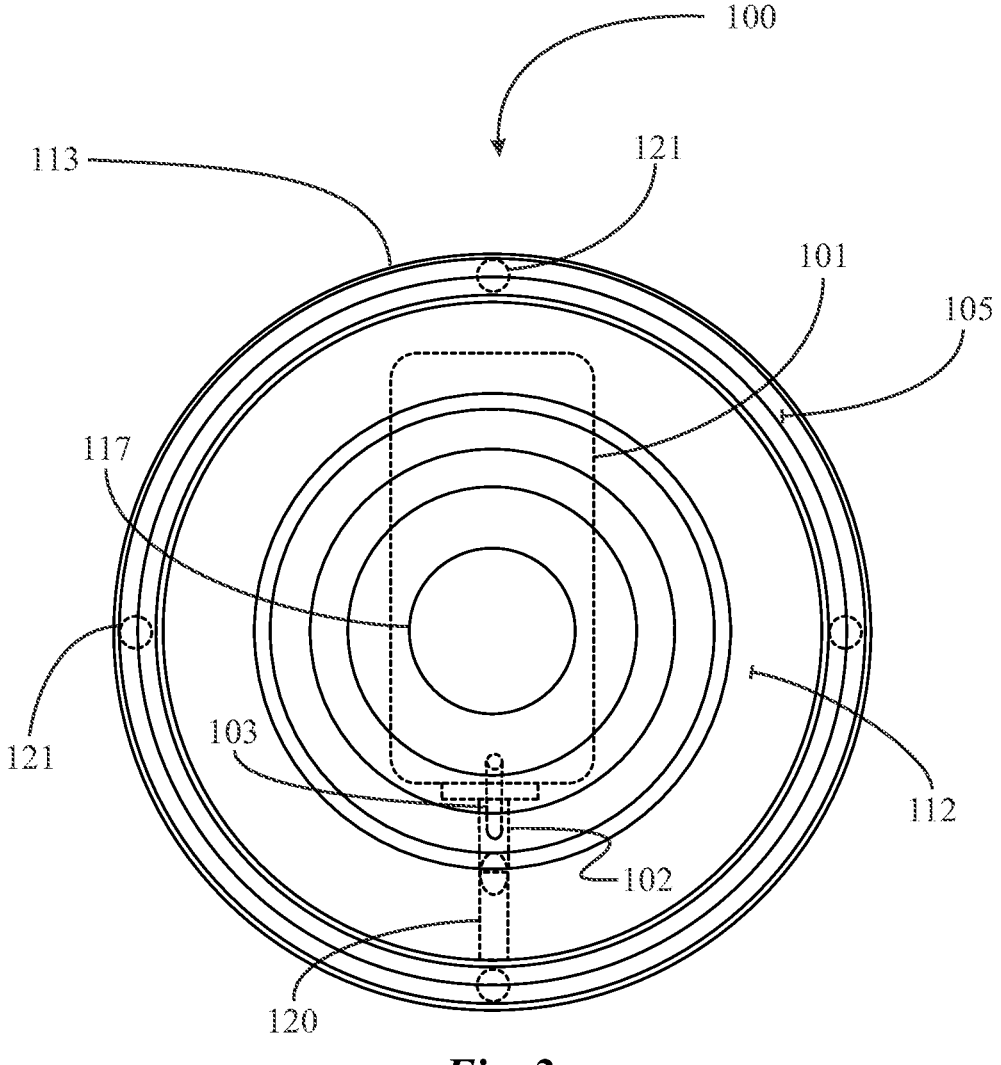
FIG. 2 is an end view of the MDI of FIG. 1 from the perspective of the mouthpiece extension.

FIG. 2 is an end view of the MDI 100 of FIG. 1 from the perspective of the mouthpiece extension referred to as spacer 112. MDI 100 is provided in an annular form referred to as a disc form. In this embodiment, ring body 106 slips into actuator ring 118. Thumb/Finger hold ring 105 is visible in this view and may be a contiguous form at the end of actuator ring 118. In this view there are four industrial springs (not illustrated) housed in the MDI assembly. Spring channels 121 are adapted to contain industrial springs 119 that extend out therefrom and are seated by spring seats 104 provided in a concentric pattern in cap 113. In one embodiment, one or more small longitudinal alignment slots may be provided in actuator ring 118 that mate with one or more small longitudinal keys formed on the outside surface of ring body 106 so that triangular form 120 will be aligned with central activator stem 102. Alignment slots and keys may also prevent ring body 106 from inadvertent rotation within actuator ring 118. In another embodiment alignment marks may be placed on ring body 106 and cap 113 so that correct alignment maybe achieved before inserting ring body 106 into actuator ring 118.

Canister 101 is depicted in broken boundary nested within ring body 106 in position to be actuated. An operator presses on hold ring 105 with thumb and fingers to compress the assembly bringing triangular form 120 up to make contact with actuator stem 102 to effect a dose release that escapes through aerosol stem 103 directly into the volume of spacer 112. Cap 113 remains in place during dosing to provide a base seat for springs 119. Cap 113 may be snapped onto ring body 106 or stretched over the ring body end. An operator may hold the MDI assembly 100 at cap 113 with one hand, and may advance actuator ring 118 by using thumbs and or fingers of the other hand against hold ring 105 with a second cap (not illustrated) removed to access spacer 112 (mouthpiece extension) and pull it out from a collapsed position. Spacer component 112 holds position when it is collapsed and holds position when extended out without depending on an internal frame or structure. This may be achieved by the material properties and construction of the device. In this embodiment, actuator form 120 has a uniform material thickness that may roughly equal the diameter of stem 102. It is noted that this view may appear the same if the spacer 112 is collapsed for storage or extended out for use.

Figures 3A, 3B, 3C:
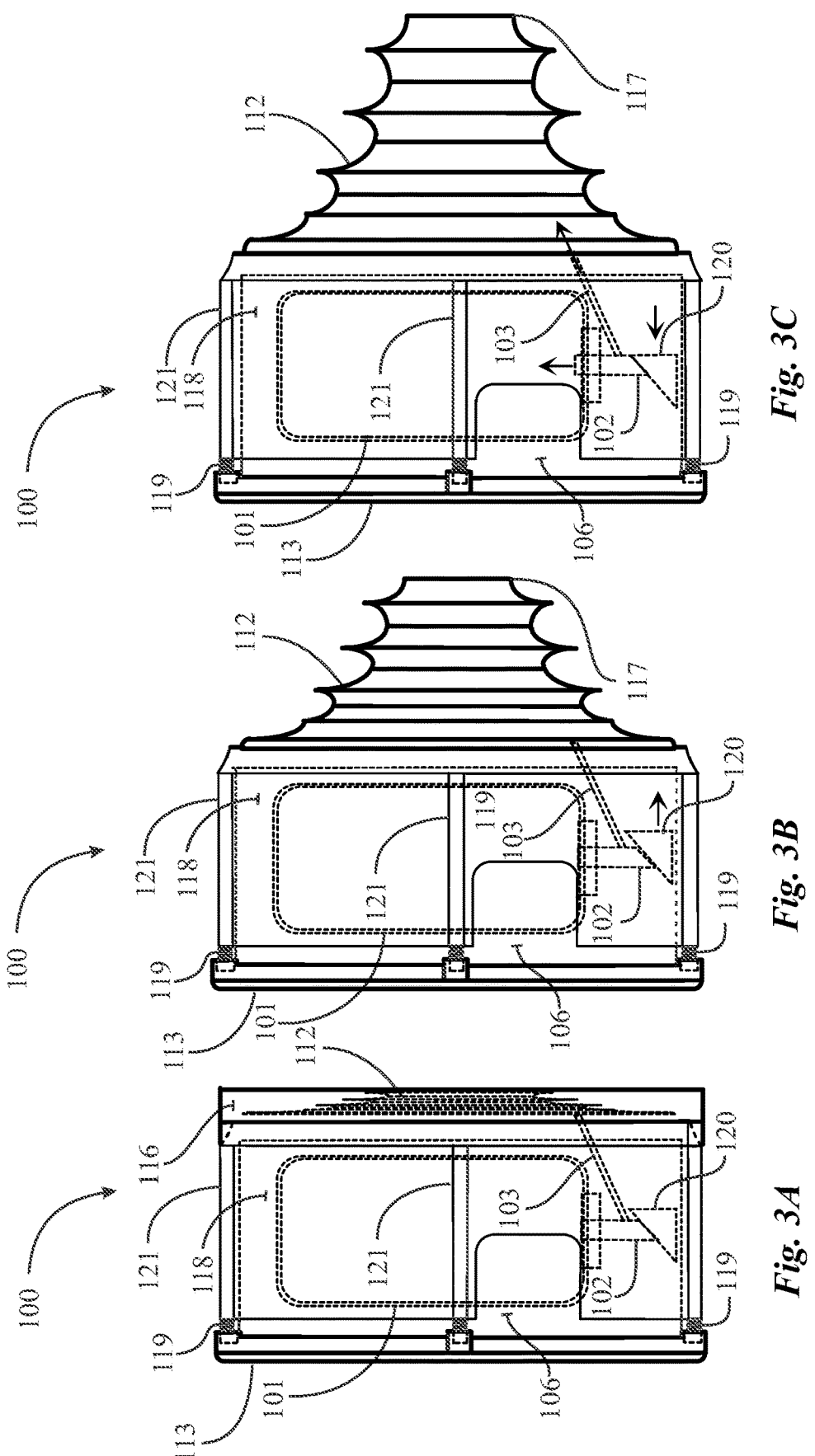
FIG. 3A is a side view of the MDI of FIG. 1 with the mouthpiece extension collapsed and capped according to an embodiment of the invention.
FIG. 3B is a side view of the MDI of FIG. 3A uncapped at one end with the mouthpiece extension partially retracted.
FIG. 3C is a side view of the MDI of FIG. 3A fully extended and in a compressed state of dose activation according to an embodiment of the invention.

FIG. 3A is a side view of MDI 100 of FIG. 1 with the mouthpiece extension collapsed and capped according to an embodiment of the invention. In this embodiment MDI 100 has spacer 112 attached and in a collapsed state. A cap 116 is provided to cover and protect the collapsed spacer 112 of MDI 100 when it is not in use. Cap 116 may be manufactured of a high food grade plastic and may include a peripheral locking rim or snap ring to secure the MDI assembly in a partially compressed state relative to equal tension in springs 119.

In one embodiment, cap 116 may be threaded on the inside diameter and may be threaded or screw locked onto that end of the MDI assembly. In a closed and capped configuration, MDI 100 is in a state of non-use. A user may store MDI 100 in this manner or may remove spacer device 112 for cleaning or for retention and cap the MDI without the spacer device 112 attached. Cap 116 must be removed to access spacer 112 to pull it out to full extension length. In this embodiment, triangular form 120 is brought forward just shy of or just flush against the angled face of canister stem 102 but not far enough to actuate canister 101 to dispense a dose. Cap 116 holds that position where the springs are equally and slightly compressed. Certain electronics embedded in ring body 106 require that a user has access to them physically or at least visually. It is noted herein that actuator ring 118 may be relieved of material so that those components described above relative to FIG. 1 are visible and or accessible to the user while MDI 100 is assembled and capped at both ends.

FIG. 3B is a side view of MDI 100 of FIG. 3A uncapped at one end with the mouthpiece extension partially retracted. In this embodiment, cap 116 is unlocked and removed to gain access to spacer 112. Once cap 116 is removed, spring tension is released and springs 119 are in a relaxed state. This retracts triangular form 120 back away from engagement with the actuator stem of canister 101 as indicated by the directional arrow leaving a small gap between the interfacing surfaces. In this embodiment, spacer 112 is partially extended out but could remain collapsed without affecting the position of triangular form 120. In one embodiment, triangular form 120 is formed on or heat welded to the inside surface of the inner ring of actuator ring 118. In an alternative embodiment, actuator ring 118 may be adapted to fit over ring body 106 whereby actuator form 120 may be presented through a material relief slot provided through the wall of ring body 106 along a longitudinal axis of the ring body. It may also be noted that material relief in the form of a longitudinal slot or slots may be provided in actuator ring 118 to allow the ring to move past canister installations points on the inside surface of ring body 106. An offset in depth between ring body 106 and actuator ring 118 provides a sufficient gap distance for compressing the MDI assembly and enabling triangular form 120 to travel far enough activate stem 102 to break seal of canister 101.

FIG. 3C is a side view of MDI 100 of FIG. 3A fully extended and in a compressed state of dose activation according to an embodiment of the invention. MDI 100 is depicted in a state of compression defining a dispense state wherein triangular form 120 has displaced the angled actuation surface of canister stem 102 thereby breaking the pressurized canister seal and releasing the medicine from canister 101. In this embodiment, an operator has removed cap 116 and fully extended spacer 112 in preparation for dosing, and has urged actuator ring 118 toward cap 113 under spring tension to activate a dose dispensed from canister 101 according to the directional arrows depicting the direction of triangular form 120 and the direction of the dispensed aerosol. In one embodiment, canister 101 carries one dose of medicine.

In another embodiment, canister 101 may be a metered dose canister that carries more than one dose of medicine under pressure. When a user releases grip on MDI assembly 100, the assembly returns to the spring-relaxed state of FIG. 3B. If the patient is not taking a second dose, the patient may then collapse spacer device 112 and compress the assembly under mild spring tension by replacing cap 116. In one embodiment, a user may grip MDI 100 with both thumbs against hold ring 105 while the fingers grasp end cap 113 using both hands to compress the assembly to dispense a dose of medicine.

Figure 4:
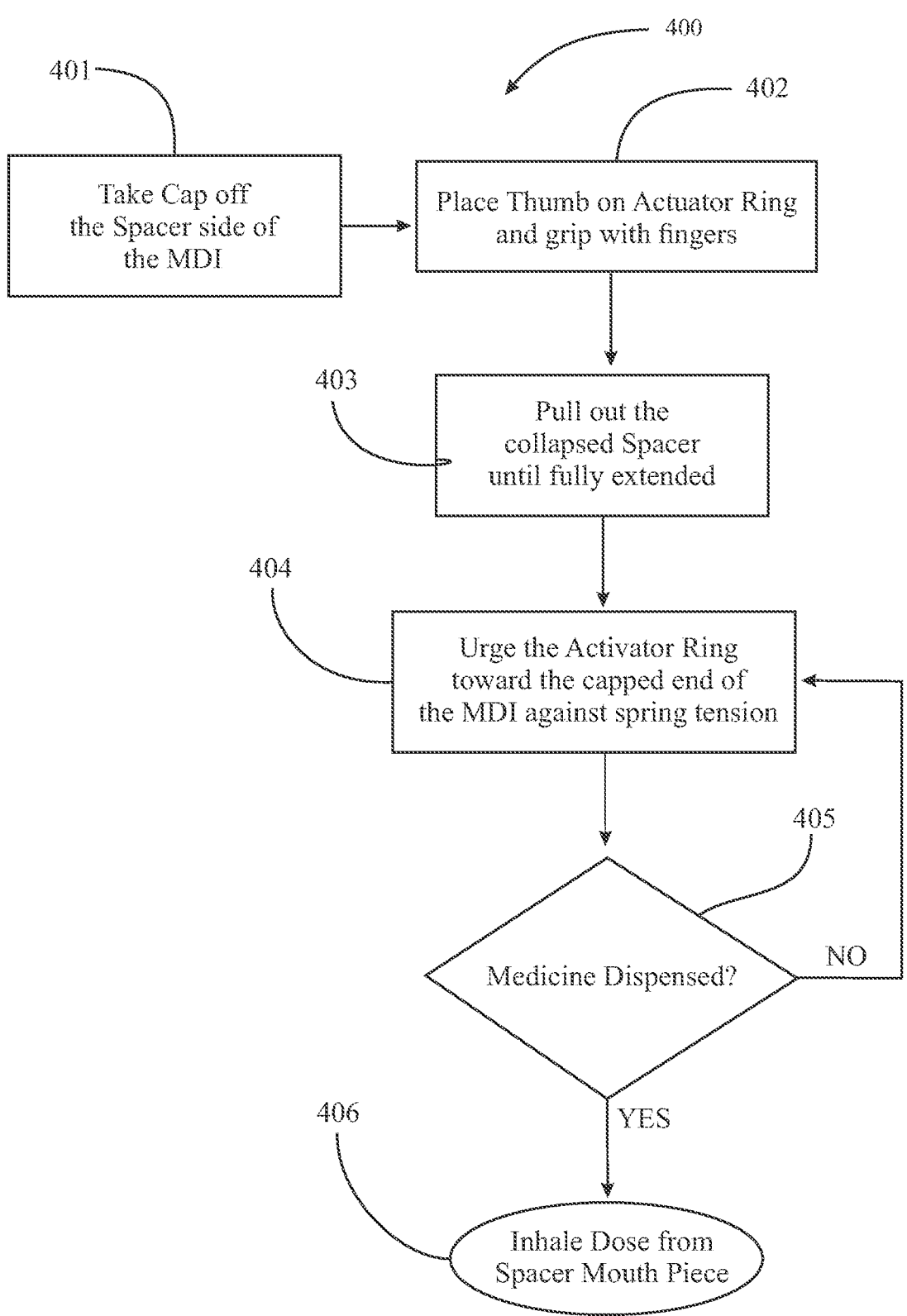
FIG. 4 is a process flow chart depicting steps for preparing the MDI for dose activation and activating a dose.

FIG. 4 is a process flow chart 400 depicting steps for preparing the MDI for dose activation and activating a dose. At step 401, a user may unlock and remove the cap referred to above as cap 116 covering the collapsed spacer 112.

Removing the cap 116 of FIG. 3A renders the MDI assembly to a relaxed spring state. At step 402, the user may grip the actuator ring using thumb and fingers. At step 403, the user may pull out the collapsed spacer 112 until it is fully extended out. In one aspect of the process flow 400, steps 402 and 403 may be reversed without departing from the spirit and scope of the invention. Spacer 112 will stay in the extended position until it is physically collapsed again. At step 404, the user may urge the activator ring 118 toward the end cap 113 under spring tension with the intent on activating a dose of medicine to be dispensed into the spacer 112.

At step 405, the user may determine if a dose was dispensed, if a dose was not dispensed at step 405, the user may repeat step 404. If at step 405 a dose of medicine was released into the internal volume of spacer 112, the user may inhale the medicine through the mouthpiece 117 of the spacer at step 406. In one aspect in step 405, determination may be made by sound emitted by the breaking canister seal. In one embodiment, one of the aforementioned LEDs 110 may light up and may be visible to the user indicating a dose was dispensed. A user may take one dose or may take more than one dose depending on the canister type and dose instruction.

Figure 5:
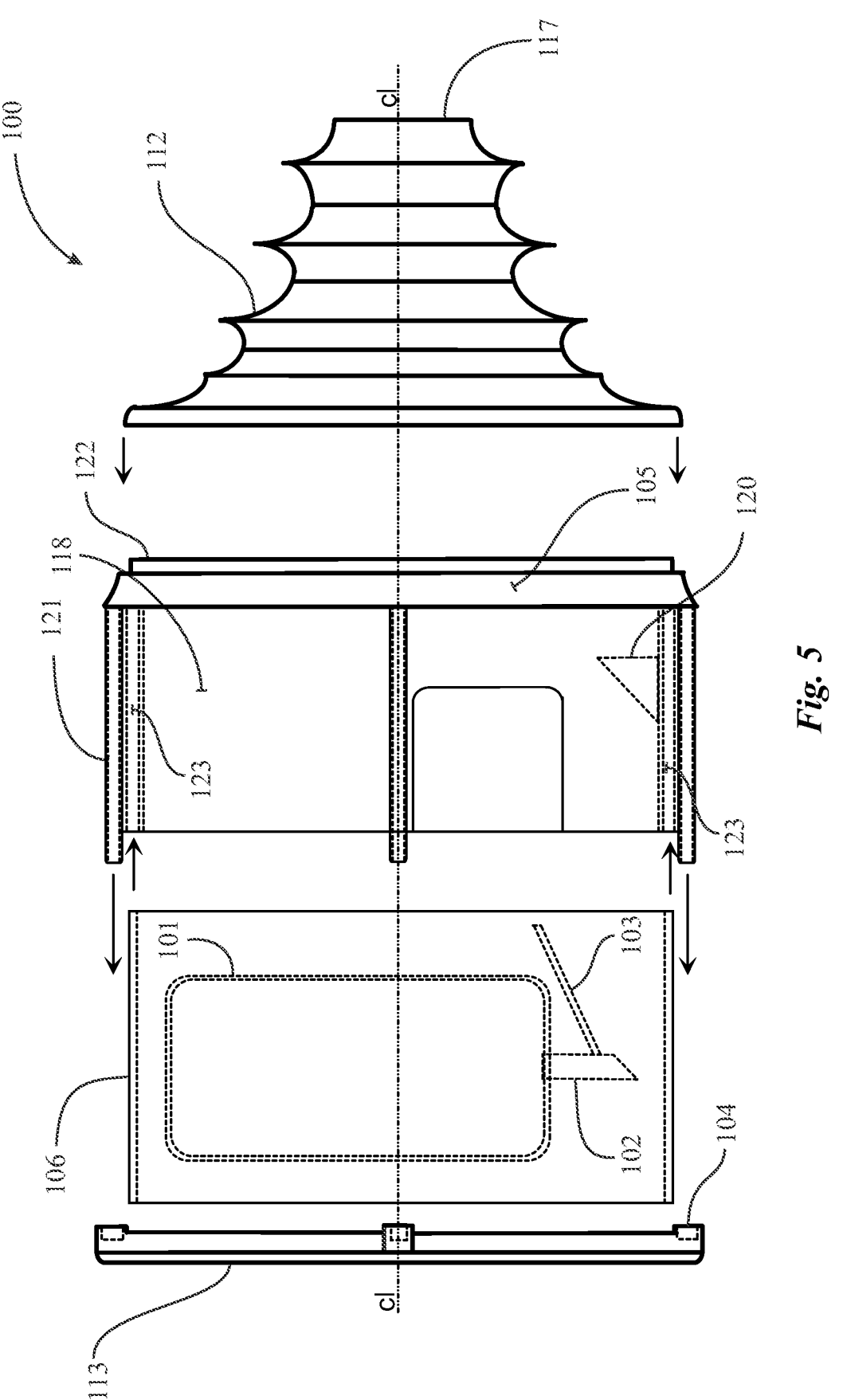
FIG. 5 is an exploded view of the portable MDI of FIG. 1.

FIG. 5 is an exploded view of portable MDI 100 of FIG. 1. In this embodiment, activator ring 118 has a double wall construction (broken lines) and is open on the end facing ring body 106. Ring body 106 is a single walled ring having a diameter that enable a user to slip into a concentric channel 123 representing the space between the two walls of the activator ring 118. Ring body 106 fits into the double walled construction of activator ring 118 according to the direction of the arrows. Activator ring 118 includes spring housings 121 formed on the outside diameter surface thereof, in this case a pattern of four housings spaced ninety degrees apart on the activator ring. Springs are not illustrated in this example but may be assumed present. Springs may be anchored at one end to the bottoms of spring housings 121 so they do not fall our of the assembly when cap 113 is removed. The springs extend outward from the open ends of spring housings 121 and may be snapped into seats 104 on end cap 113. End cap 113 also snugly fits over ring body 106.

In one embodiment, alignment is achieved between cap 113 and ring body 106 and actuator ring may be aligned via seating the springs into the cap with triangular form 120 positioned in the correct alignment with canister stem 102 of canister 101. In this embodiment, triangular form 120 is positioned on the inner most ring giving it access to stem 102. material relieve areas may be provided in actuator ring 118 to enable areas on the outside of ring body 106 to remain visible and accessible to an operator with the assembly installed. Similar material relief features including through slots may be provided to actuator ring 118 to ensure clearance around install points of canister 101. Actuator ring 118 is urged toward end cap 113 according to the direction of the arrows until the springs reach seats 104 and secured therein.

Hold ring 105 has an inward angle and may include a slight concave radius for ergonomic placement of thumb and fingers against the ring. Actuator ring 118 has a raised ring feature 122 formed concentrically on hold ring 105. Spacer 112 may be stretched to fit over ring feature 122 according to the direction of the arrows and may fit securely there over via the elastic properties of the material. In this view spacer 112 is extended. Mouthpiece 117 is the mouthpiece of the MDI assembly.

FIG. 6A is a side view of canister stem 101 of the canister of FIG. 1. Canister stem 102 is modified from a standard stem by angling the free end of the stem to about 45 degrees to create an actuation target surface for triangular actuator form 120. Canister stem 101 includes a centered bore 124 leading to a seal plane on the canister and ending just past an intersecting bore 125, which accepts insertion of the aerosol stem (removed for clarity). The medicine travels down from the canister stem through bore 124 and out into the spacer internal volume through bore 125. Bore 125 is provided at an angle off longitudinal center of canister stem 102 so that medicine is dispensed directly into the internal volume of the spacer. Vertical bore 124 and angled bore 125 may be of a standard diameter. In one embodiment, canister stem 102 is a replacement stem for a standard canister to modify the canister to work with MDI 100.

FIG. 6B is a front view of canister stem 101 of FIG. 6A. In this view, canister stem and the vertical and angled bores are aligned from the perspective of actuator 120. Bore 125 is a smaller diameter bore than bore 124 and intersects bore 124 at about a forty to forty five degree angle. FIG. 6C is a side view of canister stem 101 of FIG. 6A with the aerosol stem of FIG. 1 inserted therein. A user may insert aerosol stem 103 into bore 125 when a canister is being loaded into the ring body 106. The angle of stem 103 enable it to direct dispensed aerosol directly into the spacer. FIG. 6D is a front view of the canister stem of FIG. 6C with the aerosol stem of FIG. 6C inserted therein. When canister stem is displaced slightly upward by the triangular actuator 120 the medicine is dispensed under pressure through canister stem 102 and into aerosol stem 103 and into the internal volume of the spacer device 112 where it can be inhaled through the mouthpiece 117 of the spacer.

It will be apparent with skill in the art that the metered dose inhaler of the present invention may be provided using some or all the elements described herein. The arrangement of elements and functionality thereof relative to the metered dose inhaler of the invention is described in different embodiments each of which is an implementation of the present invention. While the uses and methods are described in enabling detail herein, it is to be noted that many alterations could be made in the details of the construction and the arrangement of the elements without departing from the spirit and scope of this invention. The present invention is limited only by the breadth of the claims below.

The invention claimed is:

1. A metered dose inhaler comprising:
a ring body open at both ends, the ring body adapted to house a pressurized canister of medicine;
an actuator ring fitting over the ring body in concentric fashion partially housing the ring body, the actuator ring having an actuator form fixed to an inside surface thereof to actuate a canister stem installed on the pressurized canister;
at least two annular spring housings fixed to an outside surface of the actuator ring, the at least two spring housings extending longitudinally thereon, in parallel, and equally spaced apart around a three hundred and sixty degree perimeter;
at least two industrial springs inserted one each into the at least two annular spring housings housing the at least two industrial springs anchored thereto;
a thumb hold ring disposed concentrically about the distal end of the actuator ring, the thumb hold ring including a concentric raised ring feature formed on a wall surface thereof;
a collapsible and extendable spacer cone installed over the raised ring feature;

a first cap for enclosing the ring body to cover the canister, the first cap including at least two spring seats for seating the at least two industrial springs; and a second cap for capping the spacer cone in a collapsed state.

2. The metered dose inhaler of claim 1, wherein the ring body has a variety of electronics embedded in the material thereof.

3. The metered dose inhaler of claim 2, wherein a portion of the variety of electronics are partially embedded in the material thereof and remain visible from the outside of the ring body.

4. The metered dose inhaler of claim 1, wherein the actuator ring has a double walled construction and fits over the ring body concentrically, the ring body partially housed by the actuator ring.

5. The metered dose inhaler of claim 4, wherein the actuator ring is urged over the ring body causing the actuator form to make contact with the canister stem to displace the canister stem into the canister breaking seal thereby actuating a dose of medicine.

6. The metered dose inhaler of claim 1, wherein the actuator form is triangular and has a uniform wall thickness.

7. The metered dose inhaler of claim 6, wherein the actuator form is disposed on the inside surface of the actuator ring in alignment with the canister stem housed inside the ring body.

8. The metered dose inhaler of claim 7, wherein the canister stem has an angled end that interfaces flush with the presented face of the triangular actuator form.

9. The metered dose inhaler of claim 1, wherein the at least two industrial springs are snapped into the spring seats on the first cap when assembled and aligned.

10. The metered dose inhaler of claim 1, wherein the first cap and the ring body each have alignment marks that provide a means for aligning the first cap to the ring body.

11. The metered dose inhaler of claim 10, wherein the actuator ring is aligned to the ring body by aligning the spring positions to the correct spring seats.

12. The metered dose inhaler of claim 1, wherein the canister stem has a first longitudinally centered bore in communication with the canister and a second bore intersecting the first bore at an acute angle the second bore accepting an aerosol stem inserted therein.

13. The metered dose inhaler of claim 2, wherein one of the variety of electronics in the ring body is a microprocessor with wireless connection capability.

14. The metered dose inhaler of claim 13, wherein the wireless connection is Bluetooth and the MDI can be located by another Bluetooth device.

15. The metered dose inhaler of claim 13, wherein the wireless connection is radio frequency identification (RFID) and the metered dose inhaler can be located by a freight on board (FOB) device.

16. The metered dose inhaler of claim 1, wherein the spacer cone includes a mouthpiece at the distal end and is stretched over the raised ring feature of the thumb hold ring.

17. The metered dose inhaler of claim 1, wherein the second cap locks over the thumb hold ring with the spacer cone collapsed.

18. The metered dose inhaler of claim 1, wherein the spacer cone is collapsed when the metered dose inhaler is idle and is extended for use.

19. The metered dose inhaler of claim 1, wherein the spacer cone has the same internal volume as the canister when extended.

20. The metered dose inhaler of claim 1, wherein the spacer cone is carried separately from the metered dose inhaler in a collapsed state and is installed by a user when required.

* * * * *